United States Patent [19]

Ehrenthal et al.

[11] 4,230,802
[45] Oct. 28, 1980

[54] UNREFINED GLUCOSE SYRUP AS SUBSTRATE BY GLUCOSE ISOMERIZING ENZYME IN PRODUCING FRUCTOSE FROM GLUCOSE

[75] Inventors: Irving Ehrenthal, University City, Mo.; Louis F. Slapshak, Belleville, Ill.; Jagdish Rajpara, St. Louis County, Mo.

[73] Assignee: Anheuser-Busch, Incorporated, St. Louis, Mo.

[21] Appl. No.: 646,629

[22] Filed: Jan. 5, 1976

[51] Int. Cl.$^3$ .............................................. C12P 19/24
[52] U.S. Cl. ...................................... 435/94; 435/99
[58] Field of Search .................. 195/31 F, 114, 66 R, 195/65, 31 R; 435/94, 99

[56] References Cited

U.S. PATENT DOCUMENTS

| 3,795,585 | 3/1974 | Suzuki et al. | 195/114 X |
| 3,813,318 | 5/1974 | Armbruster et al. | 195/31 F |
| 3,834,988 | 9/1974 | Shieh et al. | 195/31 F |
| 3,910,820 | 10/1975 | Holt et al. | 195/31 R |

FOREIGN PATENT DOCUMENTS

1295407  11/1972  United Kingdom .................. 195/31 F

OTHER PUBLICATIONS

Chemical Abstracts, 81:36632u.

*Primary Examiner*—Thomas G. Wiseman
*Attorney, Agent, or Firm*—Gravely, Lieder & Woodruff

[57] ABSTRACT

This application concerns a method of preparing high fructose syrups from unrefined high glucose syrups (produced by an acid-enzyme or enzyme-enzyme conversion) by treating the substrate with glucose isomerizing enzyme without the addition of cobalt and/or magnesium salts.

7 Claims, No Drawings

UNREFINED GLUCOSE SYRUP AS SUBSTRATE BY GLUCOSE ISOMERIZING ENZYME IN PRODUCING FRUCTOSE FROM GLUCOSE

BACKGROUND OF THE INVENTION

Fructose (levulose) is generally regarded to be substantially sweeter than glucose (dextrose) and consequently is more desirable and commands a higher price in the marketplace for that reason. However, glucose is more easily available from inexpensive sources. A practical and economical process for the conversion of glucose to fructose is therefore desirable.

There are several enzymes that convert glucose to fructose directly. Shieh, Lee and Donnelly (U.S. Pat. No. 3,834,988) have disclosed a method for isomerizing aldoses, such as glucose and xylose, to the corresponding ketoses by using enzymes produced by microorganisms of the Actinoplanes genus. Their process, however, does not achieve its best results in the absence of magnesium ion and cobaltous ion. Magnesium and cobalt salts are added to the glucose-containing substrate in the Shieh et al process to activate and heat-stabilize the isomerase.

Glucose syrups are produced from corn starch by acid conversion, acid-enzyme conversion or enzyme-enzyme conversion. Pure glucose can be produced by crystallization of glucose from a glucose syrup.

If pure glucose is used or if the glucose syrup from the aforesaid conversions is refined by filtration or filtration-carbon treatment or filtration-carbon treatment-ion exchange, a glucose syrup results which, when used as a substrate by glucose isomerizing enzymes, requires addition of magnesium and cobalt salts to produce good yields of fructose.

These fructose containing syrups must then be ion exchanged to remove the magnesium and cobalt salts from the syrup. This additional ion exchange refining step adds to the cost of the syrup product.

In the conventional process, when corn starch is hydrolyzed by acid or acid-enzyme or enzyme-enzyme processes, a material which is generally called "mud" is released from the starch matrix as a result of the gelatinization and subsequent thinning and/or saccharification. This mud is the crude water insoluble fat containing material resulting from hydrolysis.

We have discovered that if this mud is allowed to remain in the glucose-containing substrate during treatment with glucose isomerizing enzyme, the activation and stability of the glucose isomerizing enzyme are enhanced without the necessity of adding cobalt and/or magnesium salts during the isomerization reaction. If cobalt and/or magnesium salts are added during the process, they must be removed by ion exchange to produce the most satisfactory final syrup.

The glucose isomerizing activator factor or component in the mud is one or more of the fatty acid constituents. We have discovered that we can extract the mud with a fatty acid solvent and by adding the fatty acid solvent soluble fraction to a purified high glucose substrate we get an enhanced isomerization effect.

We have also discovered that when the mud remains in the substrate during the conversion of glucose to fructose by isomerizing enzyme, some of the calcium ion normally present in the substrate is complexed and is thus not available for interaction with the isomerizing enzyme. Calcium ion is usually considered to be detrimental to glucose isomerizing enzymes.

Accordingly, one of the principal objects of this invention is to provide a process for converting glucose to fructose without adding cobalt and/or magnesium salts to the substrate. Another principal object is to provide a process for producing fructose which does not require the final glucose-fructose syrup to be ion-exchanged after isomerization.

Still another object is to provide a process for producing fructose syrups from a high glucose substrate by conversion with a glucose isomerase in which the process can tolerate higher levels of calcium ion without inactivating the enzyme than conventional isomerization methods. These and other objects and advantages will become apparent hereinafter.

SUMMARY OF THE INVENTION

This invention comprises a process of converting glucose to fructose with isomerase by using unrefined high glucose syrup containing mud but without addition of cobalt and/or magnesium salts. This invention can be used with glucose isomerizing enzymes produced by organisms of the Streptomyces, Actinoplanes, Actinomyces, and Bacillus genera.

DETAILED DESCRIPTION

The mud referred to in this application is defined as the crude, water-insoluble, fat containing material resulting from the acid or enzyme hydrolysis of corn starch. The starch is about 98.5% carbohydrate and about 1.5% other material. This other material, upon acid or enzyme hydrolysis separates from the starch matrix and floats to the surface of the liquor after the solution is neutralized to pH 4.0–5.0. This mud comprises mostly fatty acids, some esterified fatty acids, some coagulated proteins, and some residual debris from the corn hull (mainly hemi-celluloses). It is a yellowish-brown material and contains a small amount of complexed mineral salts. This material is water-insoluble and partially soluble in hexane or other solvents that dissolve fat.

When the foregoing described mud is present in an unrefined high glucose syrup or added to a refined high glucose syrup from an extraneous source, either of these substrates can be treated with glucose isomerizing enzyme to convert glucose to 30–45% fructose without adding cobalt and/or magnesium salts. However, a higher level of glucose isomerase is used in the conversion because the absence of cobalt results in a decrease in enzyme stability.

We also have treated the mud with fatty acid solvents and added the fatty acid solvent soluble fraction back to a purified high glucose substrate. When glucose isomerizing enzyme is added we get an enhanced isomerization effect without adding cobalt or magnesium salts.

Therefore, whether the fatty acid solvent soluble fraction is present in the unrefined substrate, is added with the mud, or removed from the mud and added separately, it is the active material meant when we call for isomerizing a high glucose substrate in the presence of the fatty acid solvent soluble fraction.

Suitable fatty acids solvents are hexane, petroleum ether, other hydrocarbons, ethyl ether, and mixtures thereof. The terms "hexane soluble fraction" and "fatty acid solvent soluble fraction" are used interchangeably.

In any enzyme reaction, the factors of activation and stability are important. Activation is a measure of the extent of the conversion while stability is a factor of the duration of activity of the enzyme. In the glucose isomerizing reaction, magnesium seems to influence the activity and cobalt seems to influence the thermal stability. These need to be balanced in any reaction.

In the present invention, the temperature and pH are the same as described in Shieh et al U.S. Pat. No. 3,834,988. Higher temperatures tend to speed up the reaction, but lower the stability of the enzyme. The specific temperatures with Actinoplanes enzyme are about 40° C. to about 90° C., preferably 55°–75° C., and the specific pH is about 5.5 to about 9, preferably 6.5–7.5.

Table I shows the effect of cobalt and magnesium salts on isomerase activity:

TABLE I

| Activating Salt in Glucose Isomerase Activity Assay | Percent of Total Isomerase Activity |
| --- | --- |
| Cobalt and magnesium (control) | 100% |
| Magnesium only | 81.2% |
| Cobalt only | 48.4% |
| None | 23.1% |

It can be readily seen that cobalt and magnesium salts activate the isomerase.

Unrefined 95 D.E. substrate containing mud can be used to activate the isomerase, thereby eliminating the need for cobalt and magnesium salts for isomerase activation in the conversion of glucose to fructose.

In the process for producing a high fructose corn syrup using an unrefined high glucose syrup which contains mud without using additional cobalt and magnesium salts to activate the glucose isomerizing enzyme, the corn starch is initially acid hydrolyzed to about 10–15 D.E. and neutralized with sodium carbonate to a pH range of 4.0–5.0. A portion of the mud is removed by centrifugation, but the removal is never carried out to the extent that the centrifuged liquor is completely free of the crude, water-insoluble fat containing mud. The acid hydrolyzed low D.E. liquor need not be centrifuged in order that this invention be practiced. The solid material remaining in the acid converted substrate or removed by the centrifugation is called mud in this application.

The mud-containing syrup is treated with glucamylase at a temperature from about 57° C. to about 65° C. and at a pH of about 3.5 to about 4.5 for about 48 to about 72 hours at a concentration of about 0.15–0.25 glucamylase units per gram of dry solids[1] to produce a high glucose syrup of about 90% to about 93% glucose and about 93 to about 96 D.E. Suitable commercially available enzymes are G-Zyme from Enzyme Development Co. and Miles L-100 D from Miles Chemical Co.

[1] A glucamylase unit of activity is the amount of enzyme required to produce one gram of D-glucose in one hour at assay conditions of 60° C. and pH 4.2.

The unrefined high glucose syrup (95 D.E.–93% glucose) containing mud is used as the substrate for production of high fructose syrups. In the preferred reaction, glucose isomerase is added at 95 units/gram of glucose[2], and reacted at 62°–68° C. and pH 6.5–7.5. After about 18 to about 24 hours conversion, the syrup contains about 40 to about 45% fructose, about 48 to about 53% glucose, and about 7 to about 10% higher saccharides.

[2] The unit of activity is defined as the amount of enzyme required to produce one milligram of D-fructose per hour under standard assay conditions (1.0 M D-glucose substrate; 70° C.; pH 7.0; cobalt and magnesium ion present at levels of $3 \times 10^{-4}$ M and $3 \times 10^{-3}$ M, respectively).

We have further found that calcium ion present in the liquor is complexed by the mud material during the isomerization process and thus does not inactivate the isomerase.

The unrefined 95 D.E. glucose syrup containing mud can be refined by conventional processes, such as filtration or filtration-carbon treatment or filtration-carbon treatment-ion exchange. However, these refining methods do not permit advantageous use of the isomerase on these refined substrates without the addition of activating salts, i.e., cobalt and/or magnesium salts.

As hereinafter explained in more detail, an unrefined high glucose syrup which is refined by the conventional processes such as filtration or filtration-carbon treatment can be used in an isomerization process without added cobalt and/or magnesium activating salts and can achieve a satisfactory yield of fructose from glucose by practicing an alternative method of this invention. This is accomplished by adding to the refined high glucose syrup substrate at least about 0.1% dry solid (w/w) of (1) the fatty acid solvent soluble fraction, (2) mud from the centrifugation step, or (3) mud filtered from unrefined hydrolyzate. The fatty acid solvent soluble component can be obtained by hexane extraction of the centrifuged mud or acid hydrolyzate at 10–15 D.E. or acid-enzyme hydrolyzate at 93–95 D.E. More than 0.1% can be used up to about 5% dry solids (w/w) or any other practical limit. However, corn starch has only about 0.8–1% fatty acids and amounts greater than this do not add materially to the effect on glucose isomerization.

To the refined high glucose syrup containing added mud activator is added 95 glucose isomerase units/gram of glucose at a pH of about 6.5 to about 7.5, and at a temperature of about 62° C. to about 68° C. for about 18 to 24 hours.

Also, a high glucose syrup which has been ion exchanged in addition to being filtered and carbon treated can be used if the mud or fatty acid solvent soluble components of the mud are added to the substrate before isomerization. These processes using refined high glucose syrup with added mud activator do not require addition of cobalt and/or magnesium salts to effect a satisfactory conversion of glucose to fructose.

The addition of the isolated mud or its fatty acid solvent soluble components to a refined high glucose substrate in a concentration range of about 0.1% to about 5% dry solids (w/w) results in a significant increase in isomerase activity compared to control reactions where mud activator is not present. Referring to Table II it can be seen that where mud activator was used, the conversion to fructose ranged from 31% to 37%; whereas the conversion to fructose in the control sample reached a maximum of 22% under identical conversion conditions after a conversion time of 18 hours.

The activator in the mud can be isolated by means of the following process:

1. Subject the mud to solvent extraction with hexane, ethyl ether, petroleum ether, or any other solvent or solvent mixture that dissolves fatty acids.

2. Separate the water-insoluble fatty acid solvent soluble fraction which contains the isomerase activators.

3. Evaporate the solvent; the fatty acid residue is then used for activating the enzyme.

Table II shows the effect of adding mud activators obtained in the form of crude mud from the centrifugation of an acid hydrolyzed starch and in the form of hexane-soluble material obtained by hexane extraction of crude mud.

TABLE II

| High Glucose Syrups (Filtered-Carbon Refined) (Note 1) | Isomerization Time (Hours) | Percent Fructose |
| --- | --- | --- |
| A. Refined substrate-control (no mud activator) | 6<br>18 | 15.0<br>18.2 |
| B. Refined substrate, crude mud from the centrifuge added | 6<br>18 | 25.7<br>37.2 |
| C. Refined substrate, hexane soluble-water insoluble extract of crude mud from the centrifuge added | 4<br>18 | 22.5<br>35.1 |
| D. Refined substrate, hexane insoluble-water insoluble residue from crude mud from the centrifuge added | 3<br>18 | 6.5<br>19.2 |
| E. Refined substrate, hexane insoluble-water soluble fraction of crude mud from the centrifuge added | 3<br>18 | 8.1<br>22.1 |

(Note 1)
Each fraction was added back to 95 D.E. - 93% glucose substrate which was filtered and carbon refined prior to isomerization under regular conditions.

The following examples illustrate the practice of this invention and it should be understood that the invention is not limited thereto:

EXAMPLE 1

Example 1 shows the preferred process in detail using an unrefined glucose syrup which was acid converted to a low D.E. syrup and subsequently hydrolyzed by glucamylase to a high glucose syrup. The substrate was then treated with whole cell *Actinoplanes missouriensis* glucose isomerase in the presence of mud, and a high fructose syrup was produced without addition of cobalt or magnesium salts.

The substrate detailed above was produced by adjusting 23 Be' corn starch slurry to about pH 2.0 using 35% (w/v) hydrochloric acid solution. The acidified starch slurry was gelatinized and thinned at 140° C. for about 5 minutes, producing a 13.8 D.E. hydrolyzate. The liquor was cooled to 65° C. and neutralized using 14 Be' sodium carbonate solution to a pH of 4.5, and centrifuged in a Sharples DH-5 machine at 3500 rpm and at a feed rate of 150 gpm giving a retention time of 10-15 seconds. Separation of mud by centrifugation of the acid converted liquor was minimal in this low D.E. range.

The acid hydrolyzed syrup at 65° C. was adjusted to pH 4.1 and treated with 0.2 glucamylase units per gram of solids (G-Zyme from Enzyme Development Co.) for 60 hours and reached 93.6 D.E. and contained 90.0% glucose.

To this unrefined high glucose syrup, glucose isomerase was added at a level of 95 units per gram of glucose and the isomerization conducted at a temperature of 65° C. and at a pH between 7.0-7.5.
After 6 hours, 27.9% fructose had been produced.
After 18 hours, 41.7% fructose had been produced.
After 24 hours, 43.4% fructose had been produced.

EXAMPLE 2

Example 2 shows the process in detail using an unrefined glucose syrup manufactured by an enzyme-enzyme conversion. The substrate was treated with glucose isomerase in the presence of mud (from a bacterial alpha amylase hydrolysis of starch) and a high fructose syrup was produced without addition of cobalt or magnesium salts.

The substrate was prepared by diluting 23 Be' corn starch slurry to 17 Be' and adjusting the pH to 6.7 using 20% sodium carbonate solution. A bacterial alpha-amylase was added at a level of 100 units[3] per gram of solids (Dex-Lo XC from Wallerstein Co.). The starch was gelatinized and thinned at 85° C. for eight minutes. The enzyme converted liquor was subjected to high temperature treatment at 120° C. for 15 minutes. The 5.5 D.E. liquor was cooled to 88° C. A bacterial alpha-amylase was added at a level of 100 units per gram of solids using Dex-Lo XC. The hydrolyzate was held at 88° C. for one hour and reached 12.6 D.E.

[3] Modification of the SKB method (Sandstedt, Kneen and Blish) Cereal Chemistry Vol. 16, p. 712, (1939) without addition of beta-amylase.

The liquor was cooled to 60° C. and neutralized with 5% hydrochloric acid solution to pH 4.0. Glucamylase was added at a level of 0.2 glucamylase units per gram of solids and conversion contained for 48 hours. The syrup reached 96.4 D.E. and contained 94.6% glucose.

To this unrefined high glucose syrup, glucose isomerase was added at a level of 95 units per gram of glucose and the isomerization conducted at a temperature of 65° C. and at a pH of 7.0-7.5.

After 18 hours, 40.2% fructose had been produced.
After 24 hours, 41.7% fructose had been produced.

When the 96.4 D.E. unrefined high glucose syrup was refined by filtration through Whatman #1 filter paper and a Millipore filter (0.8 micron) and treated with glucose isomerase under conditions identical to the above, the isomerization reaction produced the following results:

After 18 hours, 11.5% fructose had been produced.
After 24 hours, 12.9% fructose had been produced.

EXAMPLE 3

This example compares the degree of conversion from glucose to fructose when using (1) unrefined acid-enzyme converted high glucose syrup, (2) refined acid-enzyme converted high glucose syrup to which no mud activator is added, and (3) refined acid-enzyme converted high glucose syrup to which crude mud or hexane soluble extract of mud is added to the substrate. The refining was conducted by filtration through Whatman #1 filter paper and a Millipore filter (0.8 micron). Neither cobalt nor magnesium salt was added to any of the substrates in this example. All other conditions were maintained as in Example 1.

The control sample, in which refined high glucose syrup was used, but to which no mud activator was added, showed a low percentage conversion of glucose to fructose.

Table III shows the effect of adding mud, the hexane soluble extract of mud, or the hexane soluble extract from unrefined high glucose syrup to a filtration refined high glucose substrate.

TABLE III

| Acid-Enzyme Process High Glucose Syrup | Glucose Isomerization Reaction | |
|---|---|---|
| | Conversion Hours | % Fructose |
| 1. Unrefined substrate containing mud | 18 | 38.2 |
| | 24 | 40.1 |
| 2. Refined substrate- added 0.8% dry solids (w/w) mud from the centrifuge | 18 | 35.9 |
| | 24 | 38.3 |
| 3. Refined substrate- added 2.3% dry solids (w/w) hexane soluble extract of mud from centrifuge | 18 | 34.7 |
| | 24 | 35.4 |
| 4. Refined substrate- added 0.5% dry solids (w/w) hexane soluble extract from unrefined 95 D.E. high glucose syrup | 18 | 36.5 |
| | 24 | 39.1 |
| 5. Refined substrate does not contain any mud activator | 18 | 17.1 |
| | 24 | 17.9 |

EXAMPLE 4

Example 4 illustrates the use of a carbon refined, acid-enzyme converted high glucose syrup to produce a high fructose syrup by using mud activators, without addition of cobalt or magnesium activating salts. The typical unrefined 95 D.E. syrup was refined by filtration through filter aid (Celatom FW-14S) and carbon treatment using 2.5% Darco S-51 at 60° C. for 20 minutes, filtered through Whatman #1 filter paper and finally through a Millipore filter (0.8 micron). The activating effect on the isomerizing enzyme is demonstrated when the hexane soluble extract of mud is added to the substrate. A control sample, in which carbon refined syrup containing no mud activators was used, showed a low percentage conversion of glucose to fructose. In these reactions, all conditions were maintained as in Example 1.

Table IV shows the effect of adding the hexane soluble extract of mud to a carbon refined high glucose substrate.

TABLE IV

| Acid-Enzyme Process High Glucose Syrup Carbon Refined | Glucose Isomerization Reaction | |
|---|---|---|
| | Conversion Hours | % Fructose |
| 1. Refined substrate- added 2.6% dry solids (w/w) hexane soluble extract of mud from the centrifuge | 6 | 19.5 |
| | 18 | 33.9 |
| | 24 | 38.2 |
| 2. Refined substrate contains no mud activator | 6 | 7.6 |
| | 18 | 9.6 |
| | 24 | 10.1 |

EXAMPLE 5

Example 5 illustrates the use of an ion exchanged refined, acid-enzyme converted high glucose syrup to produce a high fructose syrup by adding mud activators, without the addition of cobalt or magnesium activating salts. The typical unrefined 95 D.E. syrup was refined by filtration, carbon treatment and ion exchange, and the activating effect on the isomerizing enzyme is demonstrated when the hexane soluble extract of mud or the hexane soluble extract of unrefined 95 D.E. high glucose syrup is added to the substrate. A control sample, in which the ion exchanged refined syrup containing no mud activators was used, showed a low percentage conversion of glucose to fructose. In these reactions, all conditions were maintained as in Example 1.

Table V shows the effect of adding the hexane soluble extract of mud or of unrefined high glucose syrup to an ion exchange refined high glucose substrate.

TABLE V

| Acid-Enzyme Process High Glucose Syrups Ion Exchanged | Glucose Isomerization Reaction | |
|---|---|---|
| | Conversion Hours | % Fructose |
| 1. Refined substrate- 1.8% dry solids (w/w) hexane soluble extract of mud from the centrifuge added | 6 | 18.8 |
| | 18 | 33.3 |
| | 24 | 35.1 |
| 2. Refined substrate- 0.4% dry solids (w/w) hexane soluble extract from unrefined 95 D.E. high glucose syrup added | 6 | 27.9 |
| | 18 | 41.1 |
| | 24 | 41.1 |
| 3. Refined substrate- contains no mud activator | 6 | 13.1 |
| | 18 | 17.6 |
| | 24 | 18.4 |

What is claimed is:

1. A process for converting glucose to fructose comprising the steps of:
    A. adding to a refined high glucose substrate, a glucose isomerizing enzyme and at least about 0.1% by weight based on the weight of dry solids of the component of starch conversion mud which comprises fatty acids, esterified fatty acids, coagulated proteins, and hemi-cellulose, said refined substrate containing more than about 90% glucose and being free from extraneously added cobalt salt,
    B. continuing the conversion without adding any extraneous cobalt salt, and
    C. recovering a glucose-fructose syrup which is free from extraneously added cobalt salt and which contains at least 30% fructose.

2. A process for converting glucose to fructose comprising the steps of:
    A. adding glucose isomerizing enzyme to a high glucose substrate, which substrate comprises more than about 90% glucose and at least about 0.1% by weight on a dry solids basis of the component of starch conversion mud which comprises fatty acids, esterified fatty acids, coagulated proteins, and hemi-celluloses, said substrate being free from extraneously added cobalt salt and extraneously added magnesium salt,
    B. continuing the conversion without adding extraneous cobalt salt or extraneous magnesium salt, and
    C. recovering a glucose-fructose syrup which is free from extraneously added cobalt salt and extraneously added magnesium salt, and which contains at least 30% fructose.

3. A process for converting glucose to fructose comprising the steps of:
    A. Refining a high glucose substrate, which substrate comprises more than about 90% glucose and is free from extraneously added cobalt salt,
    B. Adding glucose isomerizing enzyme and at least about 0.1% by weight on a dry solids basis of a component of starch conversion mud which component comprises fatty acids, esterified fatty acids, coagulated proteins, and hemi-celluloses to said substrate, C. Continuing the conversion without adding any extraneous cobalt salt, and D. Recovering a glucose-fructose syrup which is free from extraneously added cobalt salt and which contains at least 30% fructose.

4. A process for converting glucose to fructose comprising the steps of:

A. Refining a high glucose substrate, which substrate comprises more than about 90% glucose and is free from extraneously added cobalt salt, B. Adding glucose isomerizing enzyme and at least about 0.1% by weight on a dry solids basis of an extract of starch conversion mud which comprises fatty acids, esterified fatty acids, coagulated proteins, and hemi-celluloses to said substrate, said extract having been derived by extracting starch conversion mud with a solvent that dissolves fat, C. Continuing the conversion without adding any extraneous cobalt salt, and D. Recovering a glucose-fructose syrup which is free from extraneously added cobalt salt and which contains at least 30% fructose.

5. The process of claim 4 wherein the solvent is selected from the group consisting of hexane or other hydrocarbons, ethyl ether, petroleum ether, and mixtures thereof.

6. A process for converting glucose to fructose comprising the steps of:

A. Adding glucose isomerizing enzyme derived from organisms of the genus Actinoplanes to a high glucose substrate, which substrate comprises more than about 90% glucose and at least about 0.1% by weight on a dry solids basis of a component of starch conversion mud which component comprises fatty acids, esterified fatty acids, coagulated proteins, and hemi-celluloses said substrate being free from extraneously added cobalt salt, B. Continuing the isomerization at a temperature of about 40° to about 90° C. and a pH of about 5.5 to about 9 without adding any extraneous cobalt salt, and C. Recovering a glucose-fructose syrup which is free from extraneously added cobalt salt and which contains at least 30% fructose.

7. A process for converting glucose to fructose comprising the steps of:

A. Adding glucose isomerizing enzyme and at least about 0.1% of a component of starch conversion mud which component comprises fatty acids, esterified fatty acids, coagulated proteins, and hemi-celluloses to a refined substrate containing more than about 90% glucose and which is free from extraneously added cobalt and magnesium salts, B. Continuing the conversion without adding any extraneous cobalt or magnesium salts, and C. Recovering a glucose-fructose syrup which is free from extraneously added cobalt and magnesium salts and which contains at least 30% fructose.

* * * * *